(12) United States Patent
Scherrer et al.

(10) Patent No.: US 8,153,849 B2
(45) Date of Patent: Apr. 10, 2012

(54) TRITYL CHLORIDE RECOVERY

(75) Inventors: Stephen C. Scherrer, Lafayette, IN (US); Anne P. Noonan, Lafayette, IN (US); Thomas K. Hutton, Dacatur, IL (US)

(73) Assignee: Tate & Lyle Technology Ltd., London (GB)

(*) Notice: Subject to any disclaimer, the term of this patent is extended or adjusted under 35 U.S.C. 154(b) by 917 days.

(21) Appl. No.: 11/999,381

(22) Filed: Dec. 4, 2007

(65) Prior Publication Data

US 2008/0234526 A1 Sep. 25, 2008

Related U.S. Application Data

(60) Provisional application No. 60/873,226, filed on Dec. 5, 2006.

(51) Int. Cl.
 C07C 17/38 (2006.01)
 C07H 11/00 (2006.01)
(52) U.S. Cl. ......................... 570/262; 536/115
(58) Field of Classification Search .................. None
 See application file for complete search history.

(56) References Cited

U.S. PATENT DOCUMENTS

| | | |
|---|---|---|
| 4,362,869 A | 12/1982 | Jenner et al. |
| 4,783,526 A | 11/1988 | O'Brien et al. |
| 4,801,700 A | 1/1989 | Tully et al. |
| 4,889,928 A | 12/1989 | Simpson |
| 4,920,207 A | 4/1990 | Sankey et al. |
| 4,977,254 A | 12/1990 | Homer et al. |

FOREIGN PATENT DOCUMENTS

| | | |
|---|---|---|
| CN | 1935822 A | 3/2007 |
| WO | WO 00/04062 | 1/2000 |
| WO | WO 2007/072496 A2 | 6/2007 |

OTHER PUBLICATIONS

International Search Report; PCT/US99/16241; Sep. 17, 1999; 3 pp.
Search and Examination Report mailed Nov. 16, 2010, for Singapore Application No. 200903719-3, 17 pgs.

*Primary Examiner* — Daniel Sullivan
*Assistant Examiner* — Clinton Brooks
(74) *Attorney, Agent, or Firm* — RatnerPrestia

(57) ABSTRACT

Methods of recovering a triarylmethyl halide from a sucrose derivatization process include the steps of
 (a) forming a mixture including
  1) a triarylmethylated sucrose derivative including at least one triarylmethyl substituent and at least one acyl substituent on the sucrose,
  2) triarylmethylated sucrose ester byproducts, and
  3) an amine;
 (b) separating from the output of step (a)
  i) the triarylmethylated sucrose derivative, and
  ii) a mixture including the triarylmethylated sucrose ester byproducts and the amine;
 (c) removing the amine from the mixture of step (b) ii);
 (d) contacting the product of step (c) with hydrogen halide to cleave triarylmethyl groups and thereby form a crude triarylmethyl halide component;
 (e) contacting the crude triarylmethyl halide component with hydrogen halide to form a purified triarylmethyl halide component; and
 (f) recovering the triarylmethyl halide from the output of step (e).

21 Claims, 1 Drawing Sheet

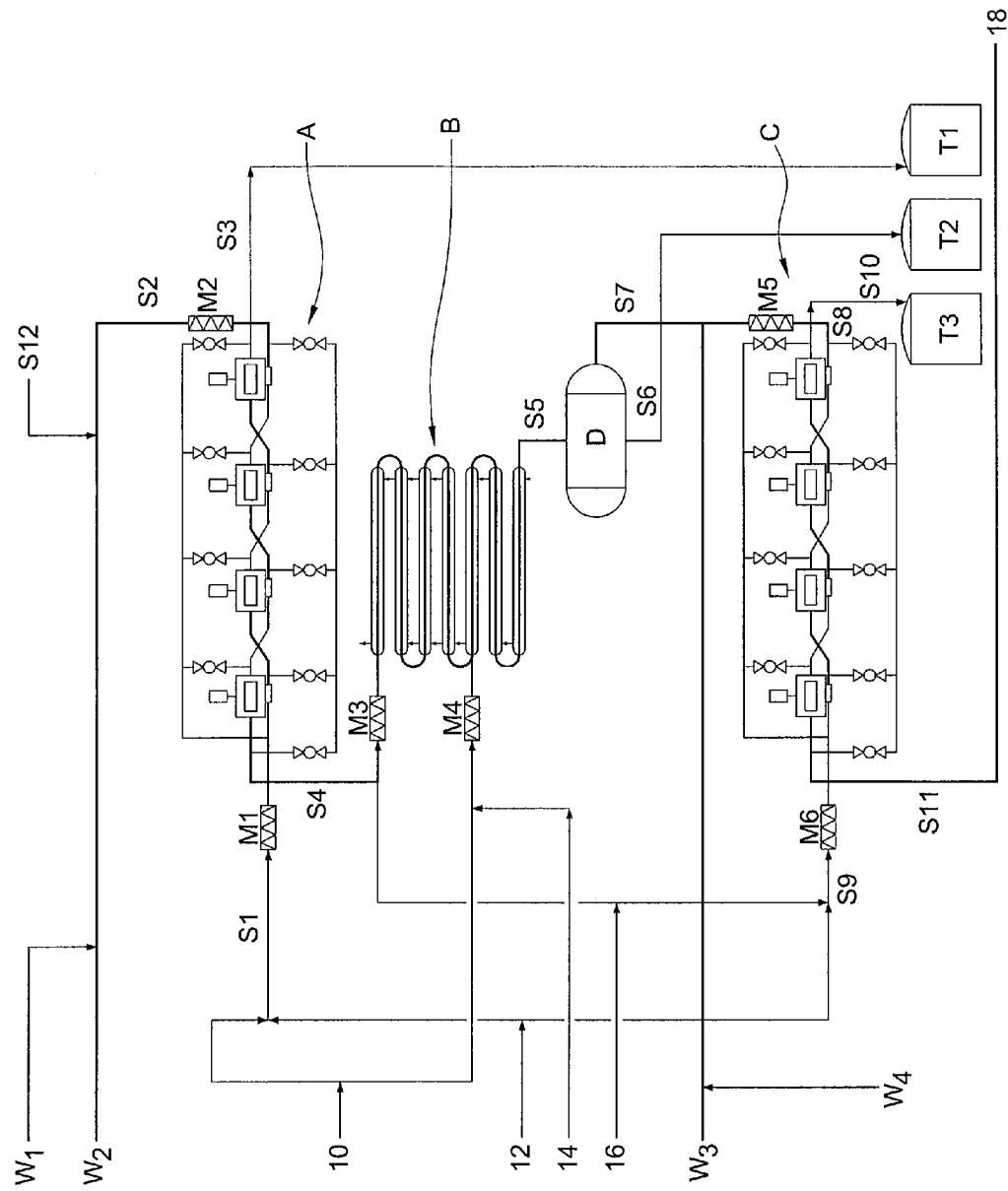

TRITYL CHLORIDE RECOVERY

CROSS REFERENCE TO RELATED APPLICATIONS

This application claims priority benefit of U.S. Provisional Patent Application No. 60/873,226, filed Dec. 5, 2006, the entire specification of which is incorporated herein by reference.

BACKGROUND OF THE INVENTION

The sucrose derivative 4,1',6'-trichloro-4,1',6'-trideoxy galactosucrose ("sucralose") is a useful and commercially important non-nutritive sweetener. One method of forming sucralose includes the following steps, wherein the use of acetyl groups is used as an example but other acyl groups (for example benzoyl) may be used instead.
 (1) Contact sucrose with a tritylating agent to form 6,1',6'-tri-O-tritylsucrose ("TRIS");
 (2) Acetylate the TRIS to obtain 6,1',6'-tri-O-tritylsucrose pentaacetate ("TRISPA");
 (3) Detritylate the TRISPA to obtain 2,3,4,3',4'-penta-O-acetylsucrose ("4-PAS");
 (4) Isomerize the 4-PAS to obtain 2,3,6,3',4'-penta-O-acetylsucrose ("6-PAS");
 (5) Chlorinate the 6-PAS to obtain 4,1',6'-trichloro-4,1',6'-trideoxygalactosucrose pentaacetate ("TOSPA"); and
 (6) Deacetylate the TOSPA to form 4,1',6'-trichloro-4,1',6'-trideoxy galactosucrose ("sucralose").

Such methods are described for example in U.S. Pat. Nos. 4,783,526; 4,801,700; 4,362,869; 4,920,207; and 4,977,254; the entirety of which are incorporated herein by reference.

The trityl groups are typically introduced via reaction with a trityl halide, such as trityl chloride. The reaction is usually promoted by the inclusion of an amine such as pyridine to neutralize the HCl liberated by the tritylation reaction. As seen above, the role of the trityl moiety is played in the first three steps of the process: (1) tritylate to form TRIS, (2) acetylate the TRIS to form TRISPA, and (3) detritylate the TRISPA to form 4-PAS.

Importantly, the overall stoichiometry of this 3-step sequence results in no net consumption of trityl groups, which are essentially "borrowed" by the sucrose for use during step 2 and released again in step 3. In practice, however, there is potential for extensive loss of trityl groups in the overall process, due to the formation of tritylated sucrose byproducts and tritylated sucrose ester byproducts (referred to herein collectively as "tritylated sucrose impurities") as will now be discussed.

The tritylation reaction and subsequent workup typically produces not only the desired tritylated product (TRIS), but also some unwanted tritylated sucrose byproducts (hereinafter "TRIS-B"). Such byproducts may for example have trityl groups in the wrong numbers and/or at the wrong positions on the sucrose molecule. Trityl alcohol is also formed from any excess trityl chloride. The TRIS is typically purified to remove the TRIS-B prior to acetylation, although it need not be. During purification of the TRIS (e.g., by crystallization, extraction, and/or chromatography), a sizable proportion of the trityl groups ends up not on the TRIS but in a waste solution, as mother liquor, raffinate or eluent fraction, in the form of the TRIS-B and/or trityl alcohol. The actual yield of correctly protected product may be mediocre. Similarly, additional byproducts (hereinafter "TRISPA-B") form during acetylation, and include for example incorrectly acetylated compounds having acetyl groups in the wrong numbers and/or in the wrong positions. If the TRIS has not been purified (i.e., TRIS-B removed) prior to acetylation, the resulting TRISPA-B may contain sucrose that has been both incorrectly tritylated and incorrectly acetylated.

From a commercial viewpoint, these inefficiencies in trityl group utilization constitute a significant barrier to use of this route to sucralose, since the tritylating agent may be 1) costly as a raw material and 2) expensive as a waste product to store or treat. Thus, methods of recovering and reusing tritylating agents from a sucralose manufacturing process would be of significant value.

BRIEF DESCRIPTION OF THE DRAWINGS

FIG. 1 is a schematic process flow diagram of a method for recovering trityl groups from a process for producing sucralose, in accordance with the invention.

SUMMARY OF THE INVENTION

In one aspect, the invention provides a method of recovering a triarylmethyl halide from a sucrose derivatization process. The method includes the steps of
 (a) triarylmethylating the sucrose in the presence of an amine to form 6,1',6'-tri-O-triarylmethylsucrose and triarylmethylated sucrose byproducts;
 (b) acylating the 6,1',6'-tri-O-triarylmethylsucrose in the presence of an amine to form a 6,1',6'-tri-O-triarylmethylsucrose pentaester and triarylmethylated sucrose ester byproducts;
 (c) separating from the output of step (b)
  i) the 6,1',6'-tri-O-triarylmethylsucrose pentaester, and
  ii) a mixture including the triarylmethylated sucrose ester byproducts and the amine of step (b);
 (d) contacting a first byproduct component including the mixture of step (c) ii) with aqueous hydrogen halide under conditions sufficient to remove the amine therefrom, thereby forming a washed byproduct component including one or more triarylmethylated sucrose impurities;
 (e) contacting the washed byproduct component with hydrogen halide to cleave triarylmethyl groups from the one or more triarylmethylated sucrose impurities and thereby form a first crude triarylmethyl halide component including triarylmethyl halide and one or more spent triarylmethyl compounds selected from the group consisting of triarylmethyl alcohol, triarylmethyl esters, and triarylmethyl ethers;
 (f) contacting the first crude triarylmethyl halide component with hydrogen halide to convert the one or more spent triarylmethyl compounds to triarylmethyl halide, thereby forming a purified triarylmethyl halide component; and
 (g) recovering the triarylmethyl halide from the output of step (f).

In another aspect, the invention provides a method of recovering a triarylmethyl halide from a sucrose derivatization process. The method includes the steps of
 (a) triarylmethylating the sucrose in the presence of an amine to form 6,1',6'-tri-O-triarylmethylsucrose and triarylmethylated sucrose byproducts;
 (b) acylating the 6,1',6'-tri-O-triarylmethylsucrose in the presence of an amine to form a 6,1',6'-tri-O-triarylmethylsucrose pentaester and triarylmethylated sucrose ester byproducts;

(c) separating from the output of step (b)
  i) the 6,1',6'-tri-O-triarylmethylsucrose pentaester, and
  ii) a mixture including the triarylmethylated sucrose ester byproducts and the amine of step (b);
(d) contacting a first byproduct component including the mixture of step (c) ii) with aqueous base under conditions sufficient to deacylate the triarylmethylated sucrose ester byproducts, and stripping the first byproduct component under conditions sufficient to remove substantially all of the amine of step (b), thereby forming a deacylated byproduct component including one or more triarylmethylated sucrose impurities;
(e) contacting the deacylated byproduct component with hydrogen halide to cleave triarylmethyl groups from the one or more triarylmethylated sucrose impurities and thereby form a first crude triarylmethyl halide component including triarylmethyl halide and one or more spent triarylmethyl compounds selected from the group consisting of triarylmethyl alcohol, triarylmethyl esters, and triarylmethyl ethers;
(f) contacting the first crude triarylmethyl halide component with hydrogen halide to convert the one or more spent triarylmethyl compounds to triarylmethyl halide, thereby forming a purified triarylmethyl halide component; and
(g) recovering the triarylmethyl halide from the output of step (f).

In yet another aspect, the invention provides a method of recovering a triarylmethyl halide from a sucrose derivatization process. The method includes the steps of
(a) forming a mixture including
  1) a triarylmethylated sucrose derivative including at least one triarylmethyl substituent and at least one acyl substituent on the sucrose,
  2) triarylmethylated sucrose ester byproducts, and
  3) an amine;
(b) separating from the output of step (a)
  i) the triarylmethylated sucrose derivative, and
  ii) a mixture including the triarylmethylated sucrose ester byproducts and the amine;
(c) contacting a first byproduct component including the mixture of step (b) ii) with aqueous hydrogen halide under conditions sufficient to remove the amine therefrom, thereby forming a washed byproduct component including one or more triarylmethylated sucrose impurities;
(d) contacting the washed byproduct component with hydrogen halide to cleave triarylmethyl groups from the one or more triarylmethylated sucrose impurities and thereby form a first crude triarylmethyl halide component including triarylmethyl halide and one or more spent triarylmethyl compounds selected from the group consisting of triarylmethyl alcohol, triarylmethyl esters, and triarylmethyl ethers;
(e) contacting the first crude triarylmethyl halide component with hydrogen halide to convert the one or more spent triarylmethyl compounds to triarylmethyl halide, thereby forming a purified triarylmethyl halide component; and
(f) recovering the triarylmethyl halide from the output of step (e).

In a further aspect, the invention provides a method of recovering a triarylmethyl halide from a sucrose derivatization process. The method includes the steps of (a) forming a mixture including
  1) a triarylmethylated sucrose derivative including at least one triarylmethyl substituent and at least one acyl substituent on the sucrose
  2) triarylmethylated sucrose ester byproducts, and
  3) an amine;
(b) separating from the output of step (a)
  i) the triarylmethylated sucrose derivative, and
  ii) a mixture including the triarylmethylated sucrose ester byproducts and the amine;
(c) contacting a first byproduct component including the mixture of step (b) ii) with aqueous base under conditions sufficient to deacylate the triarylmethylated sucrose ester byproducts, and stripping the first byproduct component under conditions sufficient to remove substantially all of the amine, thereby forming a deacylated byproduct component including one or more triarylmethylated sucrose impurities;
(d) contacting the deacylated byproduct component with hydrogen halide to cleave triarylmethyl groups from the one or more triarylmethylated sucrose impurities and thereby form a first crude triarylmethyl halide component including triarylmethyl halide and one or more spent triarylmethyl compounds selected from the group consisting of triarylmethyl alcohol, triarylmethyl esters, and triarylmethyl ethers;
(e) contacting the first crude triarylmethyl halide component with hydrogen halide to convert the one or more spent triarylmethyl compounds to triarylmethyl halide, thereby forming a purified triarylmethyl halide component; and
(f) recovering the triarylmethyl halide from the output of step (e).

DETAILED DESCRIPTION OF THE INVENTION

It has now been found that trityl groups can be effectively recovered from tritylated sucrose derivatives that are used in the preparation of 4-PAS, a valuable intermediate in the preparation of sucralose. As a preliminary matter, it should be noted that the pentabenzoate (or other pentaester) equivalent of 4-PAS may also be prepared by the methods of this invention, and ultimately converted to sucralose with recovery of trityl groups. For simplicity of discussion, the following description of the invention will refer only to 4-PAS itself, but it will be understood that the use of the pentabenzoate (or other pentaester) equivalent is also contemplated according to the invention.

Similarly, triarylmethyl groups other than trityl may be used according to the invention. For example, by judiciously modifying the substitution patterns on the aryl rings, the rate of deblocking (detritylation) can be accelerated or retarded, depending on whether the chosen substituent is electron-withdrawing, as in para-methoxy, or electron-donating as in para-methyl, groups. For simplicity of explanation, only trityl compounds will be referred to in the description of the invention, but it will be understood that the invention encompasses embodiments in which the abovementioned (and other) triarylmethyl groups are used instead.

In general, the hydrogen halide used for purposes of this invention will be HCl, although HBr may be used instead. For simplicity, the discussion hereinafter will refer to HCl.

Also for simplicity, the discussion herein will be based on the use of pyridine as the base in the tritylation and/or acetylation steps of the process, but it will be understood that any other suitable amine or other base may be used instead, such as dimethylaminopyridine, picoline, collidine, lutidine, N-methylmorpholine, triethylamine, poly(2-vinyl)pyridine or others.

The inventors have found that trityl groups may typically be expected to distribute between product (TRISPA) and byproducts (TRIS-B and TRISPA-B) in an approximately 70:30 ratio. Typically the byproducts are removed after tritylation and again after acetylation, although neither removal is absolutely required. If the impurities are removed after tritylation, this results in formation of a first waste solution we containing impurities collected during purification of TRIS, for instance as a mother liquor from crystallization or as an eluent from a chromatographic or other similar purification. These tritylated sucrose byproducts constitute at least 50 mol %, and typically at least 90 mol %, of sucrose derivatives in the $w_1$ stream. After acetylation, either in the presence or the absence of TRIS-B, the reaction mixture is worked up (typically by crystallization or chromatographic or other separation) into a product component containing TRISPA (essentially pure, but in any case constituting at least 90 mol % of the sucrose derivatives) and optionally a solvent, and a second waste solution $w_2$ that contains tritylated sucrose ester byproducts. At least 50 mol % and typically at least 90 mol % of sucrose derivatives in $w_2$ comprises such byproducts. As used herein, the term "solution" includes dispersions of any sort in a fluid, and does not imply a single phase. As used herein, the term "component" in the phrase "product component" or the like indicates that that the material being discussed constitutes at least 50 wt % of the constituents, exclusive of solvent(s). Typically, it will constitute at least 90 wt %. A "component" may, for example, be a solution of the referenced material in a solvent, or it may be the material not in a solvent.

Thus, the $w_1$ and $w_2$ waste solutions contain "wasted" trityl groups (i.e., those that do not ultimately end up on TRISPA). The other trityl groups are on the desired product (TRISPA). These must ultimately emerge as a result of detritylation to form a waste solution, $w_3$, that includes spent trityl compounds (mainly trityl alcohol, trityl ethers, and/or trityl esters) and, if HCl was used to remove the trityl protecting groups, trityl chloride. Thus all of the trityl groups end up in the individual waste solutions $w_1$, $w_2$ and $w_3$.

The waste solutions $w_1$ and $w_2$ typically contain pyridine (or other amine) in its free form and/or as pyridine hydrochloride, often in association with water and one or more of the usual solvents of organic synthesis from various parts of the overall sucralose manufacturing process, e.g., methanol, dimethyl formamide, toluene, etc. The pyridine may optionally be removed from this mixture by extraction with an aqueous acid or with water alone, leaving the tritylated sucrose byproducts intact in an organic solvent for later detritylation. Such extraction typically removes at least 80% of the pyridine and more typically at least 90%. Alternatively, the pyridine may be left in place and the entire mixture subjected to the detritylation conditions. In some embodiments anhydrous HCl is used for this purpose, directly producing crude trityl chloride.

This crude trityl chloride may subsequently be contacted with concentrated hydrochloric acid to (a) further boost the yield of trityl chloride while minimizing whatever trityl alcohol, trityl ethers and/or trityl esters might be present, and (b) provide a final polishing wash to remove any residual sucrose-derived impurities. The $w_3$ waste solution, separately generated during detritylation of TRISPA, and $w_4$ solution (filtrate from crystallization of trityl chloride), may be included in this final treatment with HCl.

Details of certain embodiments of the invention will now be provided with reference to FIG. 1. It will be understood that the details of this particular embodiment are shown by way of illustration and not as a limitation of the scope of the invention. In particular, the embodiment shown in FIG. 1 employs continuous processing systems, and using this approach tends to provide relatively lower residence times. This typically results in lower amounts of degradation and improves yield and/or purity of the recovered trityl chloride. However, batch or semi-continuous processing alternatives may be used instead, according to the invention.

The overall scheme of FIG. 1 comprises equipment for performing three broad functions: base extraction, detritylation, and activation (to regenerate trityl chloride). These functions are integrated to form a single continuous flow system, facilitating automated operation—and minimizing equipment size, internal holdups and inventory costs. It should be noted that these functions need not be integrated as shown, nor does any of the processes need to be continuous. Batch and semi-batch processes may also be used for any of the processes performed by the equipment shown in FIG. 1. However, one important consideration is the notorious lability of the sucrose-derived compounds in the system, especially their susceptibility to decomposition in the presence of heat or acid. These considerations may favor the choice of continuous rather than batch processing so as to provide the gentlest conditions possible.

Base Extraction

Base extraction vessel A separates the tritylated sucrose byproducts TRIS-B and TRISPA-B from the pyridine or other base constituent(s) of the tritylation and acetylation waste solutions, $w_1$ and $w_2$, respectively—isolating it intact in a water-immiscible organic solvent, for later detritylation. Aqueous influent stream S1 comprises a dilute HCl solution, generated by combining water (shown at 10) and commercially available concentrated 34% HCl (shown at 12) in the static mixer M1. Organic influent stream S2 includes the tritylation and acetylation waste solutions, $w_1$ and $w_2$, appropriately supplemented if necessary with a water-immiscible organic solvent S12 (such as toluene) at inline mixer M2. The extraction process is typically run at ambient temperature, although higher or lower temperatures may be used as well. The use of moderate temperatures tends to improve yield and throughput inasmuch as acid-catalyzed degradation of the various carbohydrate derivatives is minimized by cooler temperatures.

The S1 and S2 streams are vigorously intermixed in the extraction vessel A to facilitate high sequestration of the pyridine and/or other base constituent(s) or salts in the dilute acid solution. Aqueous effluent stream S3 comprises a dilute HCl solution containing in salt form the pyridine and/or other base constituent(s) originally present in waste solutions $w_1$ and/or $w_2$. Organic effluent stream S4 contains the water-immiscible organic solvent containing the highly nonpolar tritylated sucroses, substantially free of the pyridine and/or other base constituent(s). Since the S4 stream contains essentially no pyridine and no unprotected sucrose, an advantage of this embodiment is that the S4 stream may be concentrated by distillation if desired, thereby facilitating subsequent steps.

Mixers M1 and M2 may be of any type known in the art. Typically, they will be static mixers comprising a series of baffles, plates, and/or bars, angled and disposed to induce maximum radial, but minimum axial, mixing, under tightly controlled conditions of shear and flow thus affording continuous plug flow blending, with maximum cross-sectional uniformity. Other mixers may however be used, such as stirred tank mixers.

The choice of water-immiscible organic solvent may be predetermined by its pre-existence in $w_1$ and/or $w_2$ as holdovers from the recipe and/or workup of step 1 and/or step 2. Representative organic solvents from both ends of the density spectrum are encountered; from the lighter alkyl acetates, ethers, arenes, e.g., ethyl acetate, diethyl ether, toluene, respectively, to the heavier alkyl chlorides, e.g., methylene chloride, chloroform, carbon tetrachloride, etc. As used herein, the term "solvent" also refers to mixtures of solvents. The nature of the organic solvent(s) is non-critical, provided it is inert to the operating acidic conditions, and is capable of both solubilizing the trityl entities and achieving a phase distinction with aqueous stream S1. Even combinations of individual lighter, heavier and/or water-miscible, e.g., methanol, solvents are practicable, provided the composite specific gravity of organic fraction S4, is sufficiently different from the aqueous extract, S3, to provide two discrete separable phases.

Other embodiments may utilize alternate technologies for pyridine removal. For example, rather than acidifying the free pyridine portion completely to form the extractable salt form, an alternative approach is to basify the aqueous pyridine hydrochloride to form free pyridine and recover it by distillation.

The extraction vessel A, may be of any type known in the art. Advantageously, it may comprise a series of centrifugal liquid-liquid extraction units, sequentially configured to facilitate multiple countercurrent contacts between the aqueous and organic phases, thereby optimizing the overall redistribution of solutes through multiple intermediate equilibrations—that effectively compound the differences in single-stage extraction coefficients to achieve maximum separation with minimum solvent volumes. Thus, in the illustrative 4-stage concatenation of FIG. 1, the aqueous stream winds a path through extraction vessel A, progressively picking up more and more of the pyridine and/or salt from the opposing organic stream S2, until by the end of the train, when both streams ultimately emerge from extraction vessel A, substantially all of the pyridine and/or other base constituents have completely transferred from the organic S2 into the aqueous S3 stream, which is directed to aqueous salts waste tank T1.

Detritylation

Simultaneously, the organic effluent S4 from extraction vessel A, containing the highly nonpolar tritylated sucroses dissolved in the organic solvent (typically mostly toluene), and rendered substantially free of the pyridine and/or other base constituent(s), is directed to detritylation vessel B, where the bulk of the trityl removal step is actually accomplished. Numerous reagents may be applied to do this, producing variously spent trityl materials, including (a) trityl alcohol from aqueous acid such as HCl, (b) trityl ether from alcoholic acid, and (c) trityl ester from carboxylic acid. Detritylation may be catalyzed by many types of acid, such as mineral, Lewis, carboxylic, sulfonic, etc. In some embodiments, the reagent is anhydrous HCl, yielding trityl chloride directly. The other alternatives produce intermediate derivatives, requiring further chemical treatment to convert them to trityl chloride. For example, concentrated aqueous HCl may be used, thereby producing a trityl chloride/trityl alcohol mixture. Still another alternative approach is to cleave the trityl groups via hydrogenation to form triphenylmethane. In that case, trityl chloride can be regenerated by treating the triphenylmethane with $Cl_2$, with the consequently liberated HCl also forming more trityl chloride by reaction with trityl alcohol.

In the arrangement shown in FIG. 1, anhydrous HCl (shown at 16) is injected into the S4 stream, containing the tritylated sucroses, upfront of the static mixer M3. As earlier, in the case of the static mixers, M1 and M2, the internals of the static mixer M3, comprise a series of baffles, plates, and/or bars, angled and disposed to induce maximum radial, but minimum axial mixing, under tightly controlled conditions of shear and flow thus affording continuous plug flow blending, with maximum cross-sectional uniformity. Static mixers may provide the advantages of reduced maintenance, low capital cost and space efficiency—requiring a length no greater than 3-4 pipe diameters to ensure turbulent non-viscous mixing. However, other types of mixer may be used instead.

On exiting the static mixer M3, the S4 stream immediately enters a detritylation vessel B, wherein sufficient residence time is provided to cleave the trityl groups, but not so much as to invite unwanted destruction of the sucrose derivatives. Other ways of limiting the exposure of the labile sucrose derivatives to the acidic environment include (a) utilizing little more than a stoichiometric quantity of HCl, (b) equipping the reactor with an appropriately controlled coolant jacket, and (c) choosing a nonpolar solvent, from which the liberated sucrose derivatives can be immediately precipitated. The temperature of the vessel is typically maintained at 30° C. or above, and more typically at 40° C. or above. The temperature is typically no more than 70° C., and more typically no more than 55° C. Detritylation vessel B is typically a plug-flow reactor, but may be a reactor of any design.

In the case where detritylation vessel B is a plug flow reactor, it may comprise a relatively narrow bore pipe, disposed in any number of space-optimizing arrangements, most conveniently as a helically wound coil or as a multiple series of parallel tubes configured within a common shell. The latter design may be especially suitable in that it allows the common shell to provide containment for the external coolant, in a design analogous to that commonly encountered with a shell and tube heat exchanger. A further important consideration in the design of detritylation vessel B is the need to prevent excessive buildup of the precipitated sucrose derivatives on the internal walls. This may achieved by optimizing the interplay of flow-rate and cross-sectional area and by use of non-stick surfaces such as TEFLON® PTFE or the like. In situations of extreme difficulty, added benefit can be derived by ensuring the tubes are set at a slight incline to harness some gravitational assistance. Optionally, a co-current stream of water (shown at 10), optionally spiked with an organic cosolvent such as methanol (shown at 14), may be introduced at a suitably disposed point along the lower reaches of the reactor to target the frontal zone, where buildup is most likely. For example, this may be conveniently introduced through inline mixer M4, ensuring a consistent rate of cosolvent delivery.

On exiting detritylation vessel B, the reaction mixture thus predominantly comprises the free trityl chloride, dissolved in the water-immiscible organic solvent, and a complementary aqueous phase with detritylated sucrose and sucrose derivatives dissolved and/or dispersed in it. It will generally be desirable that this mixture S5 be directed to undergo immediate phase separation—not only to minimize the hydrolytic reversal of the free trityl chloride to trityl alcohol but also to protect it from adventitious contamination by any sucrose derivative decomposition products formed in the acidic aqueous environment. In the embodiment of FIG. 1, this operation is accomplished by utilizing a simple continuous decanter arrangement. Thus, the biphasic mixture S5 exiting detritylation vessel B is directed onwards into a decanter vessel, D, appropriately sized to allow sufficient settling time for separation of the phases. A weir arrangement may be appropriately located within decanter vessel D, allowing continuous draw-off of the solution of crude trityl chloride S7, from the overflow zone and of the aqueous sucrose derivative phase S6, through a bottom valve located at the base of the settling zone itself. It will be understood that other liquid-liquid extraction devices, as discussed previously in the context of extraction vessel A, may be readily substituted without departing from the invention.

Activation

Aqueous phase S6, from decanter vessel, D, is directed to sucrose derivative waste tank T2. Organic overflow stream S7 contains the free trityl chloride, inevitably in association with minor proportions of its hydrolyzed form, trityl alcohol—the latter a consequence of the aqueous environment imposed in detritylation vessel B and in decanter vessel D. This fall off in activity is repaired in activation vessel C, to which the organic overflow stream S7, is now directed—wherein the hydroxyl groups of the free trityl alcohol are resubstituted with the necessary chlorine atoms. A $w_3$ stream containing any of trityl alcohol, trityl ester, trityl ether and/or trityl chloride, substantially free of sucrose derivatives and/or decomposition products thereof, may optionally be introduced into the overall recovery system upfront of activation vessel C by combination with S7 in inline mixer M5, generating composite stream S8. The $w_3$ stream is generated as a waste solution during detritylation of the TRISPA, in those embodiments which use Lewis acid, aqueous acid, carboxylic acid and/or anhydrous HCl to perform the detritylation. Alternatively, the $w_3$ stream may be directed to a point somewhat upstream of the outlet of detritylation vessel B, or entirely prior to detritylation vessel B, to help remove whatever level of detritylated sucrose derivative(s) may be present in it.

The activation vessel C may be a reactor of any sort, but typically it will be similar in design to that previously described for extraction vessel A. Specifically, in the illustrative 4-stage concatenation of FIG. 1, aqueous stream S9 winds a path through activation vessel C, progressively picking up more and more of any sucrose derivative impurities from the opposing organic stream S8, until by the end of the train, when both streams ultimately emerge from activation vessel C, substantially all of the sucrose-derived impurities have completely transferred from organic stream S8 into aqueous stream S9, which ultimately exits the extraction chain as aqueous stream S10. The reactor is typically run at ambient temperature, although higher or lower temperatures may be used.

Organic influent stream S8 comprises the water-immiscible organic solvent and the highly nonpolar trityl chloride, trityl alcohol, trityl ether and/or trityl ester, substantially free of sucrose derivatives and/or decomposition products thereof. Aqueous influent stream S9 comprises a concentrated HCl solution, boosted, if necessary, with anhydrous HCl (shown at 16) in mixer M6. As before, this mixer may be of any type, but typically will be a static mixer. On contact, the S8 and S9 streams are vigorously intermixed in activation vessel C, to facilitate high conversion levels of the trityl alcohol, trityl ether and/or trityl ester to trityl chloride and high removal rates of any sucrose-derived impurities into the aqueous acid phase. Typically the conversion is substantially complete, but in any case is at least 50%. As a result of this process, two streams emerge. Organic effluent stream S11 incorporates the water-immiscible organic solvent and the highly nonpolar trityl chloride originally present in the organic influent stream S8, substantially free of the sucrose-derived impurities and/or decomposition products thereof. Correspondingly, aqueous effluent stream S10 contains a concentrated HCl solution containing sucrose-derived impurities and/or decomposition products thereof that were originally present in the organic influent stream S8.

Aqueous effluent stream S10, from activation vessel C, is directed to concentrated acid waste tank T3. Organic effluent S11, from activation vessel C, contains trityl chloride in high purity, typically greater than 95 wt % (i.e., at most 5 wt % of other trityl compounds in the whole of the tritylated material present) dissolved in the organic solvent, and rendered substantially free of sucrose derivatives and/or decomposition products thereof, is directed to an evaporator, crystallizer, chromatograph, or other purification device (shown at 18) to provide trityl chloride of high purity, either as a concentrated solution or in crystalline form.

The contents of T1 may be subjected to various recycling steps. For example, process solvents may be collected by distillation, leaving an aqueous solution of pyridine salts which, upon addition of a base, liberates free pyridine which can in turn be collected by distillation for reuse in the process.

Another embodiment of the invention will now be described. Although this embodiment employs batch processing systems, continuous or semi-continuous processing alternatives may be used instead according to the invention.

As part of a sucralose manufacturing process, trityl chloride is recovered from two sources: tritylated sucrose impurities, and spent trityl compounds (mainly trityl alcohol, trityl ethers such as trityl methyl ether, and/or trityl esters such as trityl acetate) produced along with trityl chloride during detritylation of TRISPA. The formation and treatment of each of these sources will now be described.

Tritylated Sucrose Impurities

In some embodiments, TRIS is not purified (i.e., tritylated sucrose byproducts are not removed) prior to acetylation, and the resulting tritylated sucrose impurities include compounds that have been both incorrectly tritylated and incorrectly acetylated. However, in other embodiments the tritylated sucrose byproducts are removed prior to acetylation. They may form a component such as described earlier herein with respect to stream $w_1$, containing tritylated sucrose byproducts, while tritylated sucrose ester byproducts are separately generated as a result of acetylation of purified TRIS as described above with respect to stream $w_2$. In such cases, the tritylated sucrose byproducts may optionally form part of the tritylated sucrose impurities component.

In either case, the tritylated sucrose impurities will typically be present as a solution in a solvent that includes some amounts of pyridine and another solvent, typically methanol. Small amounts of other solvents, for example toluene, may also be present from other parts of the sucralose manufacturing process. In a first step, the pH of the solution is raised to about 12-13 by the addition of a suitable base such as 25% sodium hydroxide, and the mixture is maintained in this pH range and heated for a time and temperature sufficient to convert any acetic acid and/or acetic anhydride (residues from TRISPA formation) to water-soluble salts and to convert any pyridine salts to free pyridine. Some amount of deacetylation of the tritylated sucrose ester byproducts also occurs at this stage, which is typically performed at about 50° C. or somewhat higher, although gentler conditions may be used.

When the first step is substantially complete, the mixture is heated to a higher temperature, typically about 90° C., to boil off most of the methanol and some of the pyridine, as well as drive the deacetylation substantially to completion. Subsequently, the mixture is sparged with steam for a time sufficient to strip out substantially all of the remaining volatile constituents, mainly pyridine and smaller amounts of methanol and toluene. This steam stripping step is typically considered to be complete when the pyridine (or other amine) content of the mixture is less than about 0.1 wt %.

A solvent (typically toluene, although other water-immiscible solvents may be used) is then added to the mixture, resulting in a solvent phase that contains most of the trityl groups, largely in the form of tritylated sucroses but also sometime containing smaller amounts of trityl alcohol, and an aqueous phase that largely contains water-soluble salts such as sodium acetate. The phases are separated, the aqueous phase is extracted with additional toluene and then discarded. The toluene phases are combined for subsequent detritylation of the tritylated sucroses contained therein.

Detritylation may be effected by contacting the toluene phase with aqueous HCl, typically at about 32 wt % concentration, to cleave the trityl groups off of the tritylated sucrose esters and form trityl alcohol and some-amount of trityl chloride. If desired, the formation of trityl chloride may be driven to a greater degree of completion by using a more concentrated HCl, around 35 wt %, or by treating the toluene phase with anhydrous HCl. Any of these treatments may typically be performed at approximately ambient temperatures, although somewhat higher or lower temperatures may be used. Generally, these steps will be performed in a range from about 15° C. to about 30° C. The result is a toluene solution of trityl chloride of intermediate purity, which typically undergoes a final conversion to high grade trityl chloride as will be described further below. Prior to such conversion, in some embodiments the crude trityl chloride is first combined with crude trityl chloride derived from detritylation of TRISPA to form 4-PAS, as will now be described.

Spent Trityl Compounds

Spent trityl compounds (mainly trityl alcohol, trityl ethers, and/or trityl esters) are produced along with trityl chloride during detritylation of TRISPA, which is typically performed by contacting the TRISPA with anhydrous HCl in a solvent (typically toluene). Typically, when anhydrous HCl is used for detritylation, the trityl groups are mostly in the form of trityl chloride, with trityl alcohol, ethers or esters contributing a lesser amount. The spent trityl compounds and trityl chloride are present in toluene solution, and the solution is typically washed with 32 wt % aqueous HCl to remove water-soluble components such as sucrose derivatives and residual amounts of amines from elsewhere in the sucralose manufacturing process. Ambient temperatures are typically used for the wash, and anywhere in a range of about 15° C. to about 30° C. is generally workable although other temperatures may be used. The result is a toluene solution of a second crude trityl chloride, which may be concentrated by distillation or vacuum stripping and then converted to high grade trityl chloride as will now be described, either alone or in combination with the crude trityl chloride obtained from the tritylated sucrose impurities as described above.

Preparation of High Grade Trityl Chloride

Crude trityl chloride (as a solution in toluene), prepared as described above, may then be converted to high grade trityl chloride. Also included in the feed may be mother liquor from final crystallization of trityl chloride. In some embodiments, it may be helpful to first treat the crude material with activated carbon, to improve overall purity, but this is not required. The conversion to high grade trityl chloride may be performed by contacting the solution with concentrated aqueous HCl (typically 35-37 wt %). The use of anhydrous HCl may also be used to complete the conversion. The resulting trityl chloride has a purity typically greater than 95 wt % (i.e., at most 5 wt % of other trityl compounds in the whole of the tritylated material present) dissolved in the organic solvent. This solution may be concentrated by stripping at an elevated temperature (typically about 50° C. to about 70° C., and typically under vacuum) to a concentration of about 50 to 55 wt %, followed by cooling to allow the trityl chloride to precipitate out as crystals of high purity, typically at least 98 wt %, which may be recovered by centrifuging or filtration. Typically, the cooling is to a temperature in a range of about 0° C. to about 20° C. The crystalline product may be used as is or dried to remove solvent, and the mother liquor may be recycled as mentioned above.

More generally, any of the foregoing procedures may be applied to the recovery of trityl chloride from other sucrose derivatization processes, especially those for making sucralose. One exemplary application is in a process for making sucralose via tritylated and acylated intermediates other than those described hereinabove, for example using a synthetic route such as that disclosed in Chinese Patent Application Disclosure No. CN 1935822 A, published Mar. 28, 2007, incorporated herein by reference. That process begins with a sucrose 4,6-orthoester, prepared for example as described in U.S. Pat. No. 4,889,928, incorporated herein by reference. Reaction of the orthoester with trityl chloride in the presence of an amine (such as pyridine) provides the corresponding 1', 6' ditritylated orthoester, which is then acetylated with acetic anhydride at the 2,3,3' and 4' positions (also in the presence of an amine, such as pyridine) to protect all of the remaining hydroxyl groups. Partial hydrolysis of that product with 1/5 water/acetic acid provides 2,3,6,3',4'-penta-O-acetylsucrose (6-PAS), which may then be converted to sucralose by known methods.

According to the present invention, manufacture of sucralose by such a route may also include isolating one or more of the intermediates by crystallization, chromatography, or other means, in the process of which a mixture including tritylated sucrose ester byproducts and the amine may be formed. Such a mixture may be treated by the methods described previously herein to recover trityl chloride. Trityl chloride may also be recovered from the step of converting the tritylated and acetylated orthoester to 2,3,6,3',4'-penta-O-acetylsucrose, using the same techniques described previously herein in relation to recovering trityl chloride from trityl groups freed by detritylating TRISPA to form 2,3,4,3',4'-penta-O-acetylsucrose.

Thus, in general, the invention provides methods of recovering trityl chloride that include:
 (a) forming a mixture comprising
   1) a tritylated sucrose derivative comprising at least one trityl substituent and at least one acyl substituent on the sucrose,
   2) tritylated sucrose ester byproducts, and
   3) an amine; and
 (b) separating from the output of step (a)
   i) the tritylated sucrose derivative, and
   ii) a mixture comprising the tritylated sucrose ester byproducts and the amine.

In one embodiment, the method then includes contacting a byproduct component comprising the mixture of step (b) ii) with aqueous hydrogen halide under conditions sufficient to remove the amine therefrom, thereby forming a washed byproduct component comprising one or more tritylated sucrose impurities. Subseqently the washed byproduct component is contacted with hydrogen halide to cleave trityl groups from the one or more tritylated sucrose impurities and thereby form a crude trityl halide component comprising trityl halide and one or more spent trityl compounds selected from the group consisting of trityl alcohol, trityl esters, and trityl ethers. The crude trityl halide component is then contacted with hydrogen halide to convert the one or more spent trityl compounds to trityl halide, thereby forming a purified trityl halide component, after which the trityl halide is recovered.

In another embodiment, the method includes contacting a byproduct component comprising the mixture of step (b) ii) with aqueous base under conditions sufficient to deacylate the tritylated sucrose ester byproducts, and stripping the first byproduct component under conditions sufficient to remove substantially all of the amine, thereby forming a deacylated byproduct component comprising one or more tritylated sucrose impurities. This component is then contacted with hydrogen halide to cleave trityl groups (and any orthoester groups) from the one or more tritylated sucrose impurities and thereby form a crude trityl halide component comprising trityl halide and one or more spent trityl compounds selected from the group consisting of trityl alcohol, trityl esters, and trityl ethers. The crude trityl halide component is then contacted with hydrogen halide to convert the one or more spent trityl compounds to trityl halide, thereby forming a purified trityl halide component, and subsequently recovering the trityl halide.

Although the invention is illustrated and described herein with reference to specific embodiments, it is not intended that the subjoined claims be limited to the details shown. Rather, it is expected that various modifications may be made in these details by those skilled in the art, which modifications may still be within the spirit and scope of the claimed subject matter and it is intended that these claims be construed accordingly.

What is claimed:

1. A method of recovering a triarylmethyl halide from a sucrose derivatization process, comprising the steps of
  (a) triarylmethylating the sucrose in the presence of an amine to form 6,1',6'-tri-O-triarylmethylsucrose and triarylmethylated sucrose byproducts;
  (b) acylating the 6,1',6'-tri-O-triarylmethylsucrose in the presence of an amine to form a 6,1',6'-tri-O-triarylmethylsucrose pentaester and triarylmethylated sucrose ester byproducts;
  (c) separating from the output of step (b) as separate distinct components
    i) the 6,1',6'-tri-O-triarylmethylsucrose pentaester, and
    ii) a mixture comprising the triarylmethylated sucrose ester byproducts and the amine of step (b);
  (d) contacting a first byproduct component comprising the mixture of step (c) ii) with aqueous hydrogen halide under conditions sufficient to remove the amine therefrom, thereby forming a washed byproduct component comprising one or more triarylmethylated sucrose impurities;
  (e) contacting the washed byproduct component with hydrogen halide to cleave triarylmethyl groups from the one or more triarylmethylated sucrose impurities and thereby form a first crude triarylmethyl halide component comprising triarylmethyl halide and one or more spent triarylmethyl compounds selected from the group consisting of triarylmethyl alcohol, triarylmethyl esters, and triarylmethyl ethers;
  (f) contacting the first crude triarylmethyl halide component with hydrogen halide to convert the one or more spent triarylmethyl compounds to triarylmethyl halide, thereby forming a purified triarylmethyl halide component; and
  (g) recovering the triarylmethyl halide from the output of step (f).

2. The method of claim 1, wherein step (b) is performed in the presence of the triarylmethylated sucrose byproducts of step (a) and wherein said triarylmethylated sucrose byproducts are acylated to form a portion of the triarylmethylated sucrose ester byproducts.

3. The method of claim 1, wherein the first byproduct component further comprises the triarylmethylated sucrose byproducts of step (a) and wherein the contacting of step (d) additionally cleaves triarylmethyl groups therefrom.

4. The method of claim 1, wherein the first byproduct component further comprises the amine of step (a) and wherein the contacting of step (d) further removes said amine of step (a) from the first byproduct component.

5. The method of claim 1, wherein triarylmethyl is trityl.

6. The method of claim 1, further comprising contacting the 6,1',6'-tri-O-triarylmethylsucrose pentaester with an acid under conditions sufficient to remove the triarylmethyl groups therefrom and thereby form 2,3,4,3',4'-penta-O-acylsucrose and a second crude triarylmethyl halide component comprising triarylmethyl halide and one or more spent triarylmethyl compounds selected from the group consisting of triarylmethyl alcohol, triarylmethyl esters and triarylmethyl ethers, and subsequently separating the second crude triarylmethyl halide component from the 2,3,4,3',4'-penta-O-acylsucrose and contacting it with hydrogen halide to convert the one or more spent triarylmethyl compounds to triarylmethyl halide.

7. The method of claim 6, wherein the acid is anhydrous hydrogen halide.

8. The method of claim 6, wherein the second crude triarylmethyl halide component is mixed with the first crude triarylmethyl halide component after step (e) and before step (f).

9. The method of claim 8, wherein the hydrogen halide in step (f) is aqueous.

10. The method of claim 8, wherein the hydrogen halide in step (f) is anhydrous.

11. The method of claim 6, wherein the second crude triarylmethyl halide component is mixed with the washed byproduct component after step (d) and before or during step (e).

12. The method of claim 11, wherein the hydrogen halide in step (f) is aqueous.

13. The method of claim 11, wherein the hydrogen halide in step (f) is anhydrous.

14. The method of claim 6, further comprising converting the 2,3,4,3',4'-penta-O-acylsucrose to sucralose.

15. The method of claim 1, wherein halide is chloride.

16. The method of claim 1, wherein halide is bromide.

17. The method of claim 1, wherein the step of acylating comprises acetylating.

18. The method of claim 1, wherein the step of acylating comprises benzoylating.

19. The method of claim 1, wherein the amine is pyridine in step (a), step (b), or both.

20. A method of recovering a triarylmethyl halide from a sucrose derivatization process, comprising the steps of
  (a) forming a mixture comprising
    1) a triarylmethylated sucrose derivative comprising at least one triarylmethyl substituent and at least one acyl substituent on the sucrose,
    2) triarylmethylated sucrose ester byproducts, and
    3) an amine;
  (b) separating from the output of step (a) as separate distinct components
    i) the triarylmethylated sucrose derivative, and
    ii) a mixture comprising the triarylmethylated sucrose ester byproducts and the amine;

(c) contacting a first byproduct component comprising the mixture of step (b) ii) with aqueous hydrogen halide under conditions sufficient to remove the amine therefrom, thereby forming a washed byproduct component comprising one or more triarylmethylated sucrose impurities;

(d) contacting the washed byproduct component with hydrogen halide to cleave triarylmethyl groups from the one or more triarylmethylated sucrose impurities and thereby form a first crude triarylmethyl halide component comprising triarylmethyl halide and one or more spent triarylmethyl compounds selected from the group consisting of triarylmethyl alcohol, triarylmethyl esters, and triarylmethyl ethers;

(e) contacting the first crude triarylmethyl halide component with hydrogen halide to convert the one or more spent triarylmethyl compounds to triarylmethyl halide, thereby forming a purified triarylmethyl halide component; and (f) recovering the triarylmethyl halide from the output of step (e).

21. The method of claim 20, further comprising converting the triarylmethylated sucrose derivative to sucralose.

* * * * *